(12) United States Patent
Suh

(10) Patent No.: US 6,422,082 B1
(45) Date of Patent: Jul. 23, 2002

(54) LASER SHOCK PEENING QUALITY ASSURANCE BY ULTRASONIC ANALYSIS

(75) Inventor: Ui Won Suh, Cincinnatti, OH (US)

(73) Assignee: General Electric Company, Schenectady, NY (US)

( * ) Notice: Subject to any disclaimer, the term of this patent is extended or adjusted under 35 U.S.C. 154(b) by 57 days.

(21) Appl. No.: 09/723,264

(22) Filed: Nov. 27, 2000

(51) Int. Cl.$^7$ .............................................. G01N 29/04
(52) U.S. Cl. ...................... 73/624; 73/11.02; 73/632; 73/646; 73/602
(58) Field of Search .......................... 73/646, 602, 620, 73/627, 628, 624, 632, 11.02; 356/35.5; 382/199, 261

(56) References Cited

U.S. PATENT DOCUMENTS

| | | | |
|---|---|---|---|
| 4,627,096 A | 12/1986 | Grattoni et al. ................. 382/8 |
| 4,896,278 A | * 1/1990 | Grove .......................... 702/36 |
| 5,563,962 A | * 10/1996 | Peters et al. ................. 382/261 |
| 5,773,721 A | 6/1998 | Bashyam ....................... 73/596 |
| 5,774,177 A | 6/1998 | Lane ........................... 348/88 |
| 5,948,293 A | 9/1999 | Sommers et al. ........ 219/121.85 |
| 5,951,790 A | 9/1999 | Mannava et al. ............ 148/510 |
| 5,974,889 A | * 11/1999 | Trantow ....................... 73/624 |
| 5,987,991 A | 11/1999 | Trantow et al. ................ 73/624 |
| 6,021,222 A | 2/2000 | Yamagata .................... 382/199 |
| 6,094,260 A | 7/2000 | Rockstroh et al. .......... 356/35.5 |
| 6,094,508 A | 7/2000 | Acharya et al. ............. 382/199 |
| 6,130,400 A | 10/2000 | Rockstroh ................ 219/121.6 |
| 6,155,104 A | * 12/2000 | Suresh et al. .................. 73/81 |
| 6,254,703 B1 | * 7/2001 | Sokol et al. ................. 148/508 |
| 6,311,135 B1 | * 10/2001 | Suresh et al. ................. 702/43 |
| 6,333,488 B1 | * 12/2001 | Lawrence et al. ...... 219/121.84 |

* cited by examiner

Primary Examiner—Hezron Williams
Assistant Examiner—Jacques Saint-Surin
(74) Attorney, Agent, or Firm—V. G. Ramaswamy; Steven J. Rosen

(57) ABSTRACT

A method for quality control testing of a laser shock peening process of a production workpiece includes (a) ultrasonically scanning at least a portion of a laser shock peened surface on the workpiece wherein a region having deep compressive residual stresses imparted by the laser shock peening process extends into the workpiece from the laser shock peened surface, (b) digitizing a signal derived from the scanning and forming a digitized image of intensity values from the scanning, (c) calculating at least one statistical function value for a plurality of points of the digitized image of the workpiece based on the intensity values, and (d) comparing the statistical function value to a pass or fail criteria for quality assurance of the laser shock peening process or accepting or rejecting the workpiece.

19 Claims, 8 Drawing Sheets

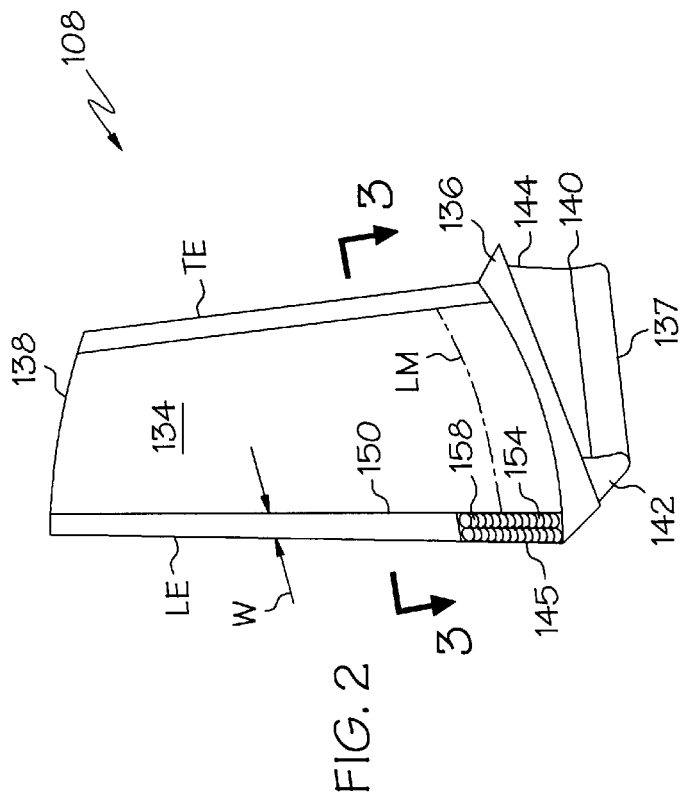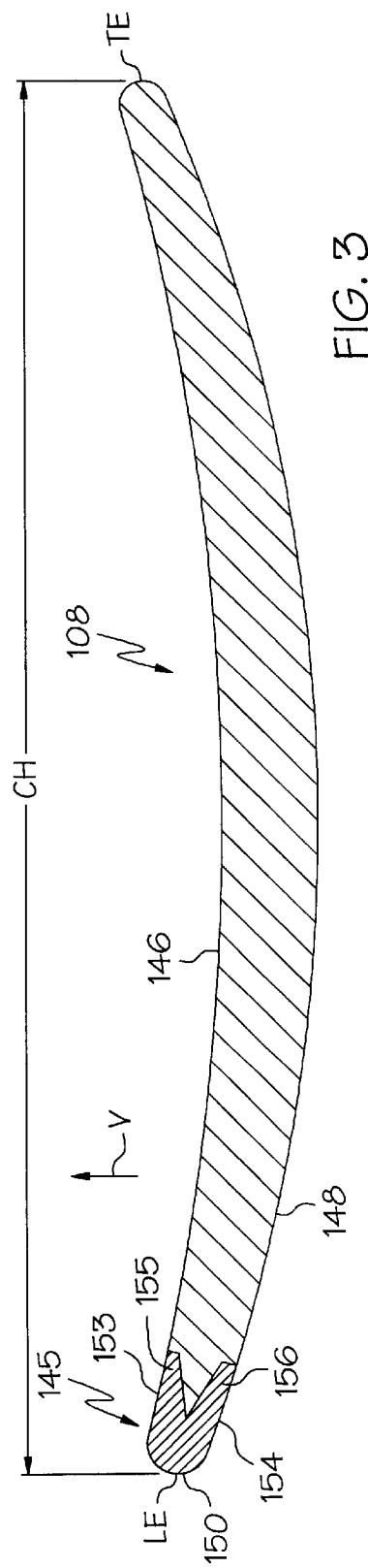

$$MM(k) = \frac{1}{X}\sum_{x=1}^{X} d_k(x)$$

$$SDM(k) = \sqrt{\frac{1}{X}\sum_{x=1}^{X}(d_k(x) - MM(k))^2}$$

$$MV(x) = \frac{1}{K}\sum_{k=1}^{K} d_k(x)$$

$$SDV(x) = \sqrt{\frac{\sum_{x=1}^{X}(d_k(x) - MV(x))^2}{X}}$$

FIG. 8

$$F1 = \frac{1}{K}\sum_{k=1}^{K} MM(k) = \frac{1}{K}\sum_{k=1}^{K}\left[\frac{1}{X}\sum_{x=1}^{X} d_k(x)\right]$$

$$F2 = \frac{1}{K}\sum_{k=1}^{K} SDM(k) = \frac{1}{K}\sum_{k=1}^{K}\left[\sqrt{\frac{1}{X}\sum_{x=1}^{X}(d_k(x) - MM(k))^2}\right]$$

$$F3 = \frac{1}{X}\sum_{x=1}^{X} SDV(x) = \frac{1}{X}\sum_{x=1}^{X}\left[\sqrt{\frac{\sum_{k=1}^{K}(d_k(x) - MV(x))^2}{K}}\right]$$

$$F4 = \frac{\sum_i \sum_j (d_{u,v} * w_{u,v})}{N}$$

FIG. 9

$$W_{u,v} = \begin{vmatrix} W_{1,1} & 51 W_{1,2} & W_{1,3} \\ W_{2,1} & W_{2,2} & W_{2,3} \\ W_{3,1} & W_{3,2} & W_{3,3} \end{vmatrix} = \begin{vmatrix} -1 & -2 & -1 \\ 0 & 0 & 0 \\ 1 & 2 & 1 \end{vmatrix}$$

LASER SHOCK PEENING QUALITY ASSURANCE BY ULTRASONIC ANALYSIS

BACKGROUND OF THE INVENTION

1. Field of the Invention

This invention relates to quality assurance methods used for quality assurance for laser shock peening and, more particularly, for ultrasonic testing and statistical analysis of laser shock peened surfaces for quality assurance of a production laser shock peening process.

2. Discussion of the Background Art

Laser shock peening or laser shock processing, as it is also referred to, is a process for producing a region of deep compressive residual stresses imparted by laser shock peening a surface area of a workpiece. Laser shock peening typically uses multiple radiation pulses from high power pulsed lasers to produce shock waves on the surface of a workpiece similar to methods disclosed in U.S. Pat. No. 3,850,698, entitled "Altering Material Properties"; U.S. Pat. No. 4,401,477, entitled "Laser Shock Processing"; and U.S. Pat. No. 5,131,957, entitled "Material Properties". Laser shock peening, as understood in the art and as used herein, means utilizing a laser beam from a laser beam source to produce a strong localized compressive force on a portion of a surface by producing an explosive force by instantaneous ablation or vaporization of a painted or coated or uncoated surface. Laser peening has been utilized to create a compressively stressed protection layer at the outer surface of a workpiece which is known to considerably increase the resistance of the workpiece to fatigue failure as disclosed in U.S. Pat. No. 4,937,421, entitled "Laser Peening System and Method". These methods typically employ a curtain of water flowed over the workpiece or some other method to provide a confining medium to confine and redirect the process generated shock waves into the bulk of the material of a component being LSP'D to create the beneficial compressive residual stresses.

Laser shock peening is being developed for many applications in the gas turbine engine field, some of which are disclosed in the following U.S. Pat. Nos.: 5,756,965 entitled "ON THE FLY LASER SHOCK PEENING"; U.S. Pat. No. 5,591,009, entitled "Laser shock peened gas turbine engine fan blade edges"; U.S. Pat. No. 5,569,018, entitled "Technique to prevent or divert cracks"; U.S. Pat. No. 5,531,570, entitled "Distortion control for laser shock peened gas turbine engine compressor blade edges"; U.S. Pat. No. 5,492,447, entitled "Laser shock peened rotor components for turbomachinery"; U.S. Pat. No. 5,674,329, entitled "Adhesive tape covered laser shock peening"; and U.S. Pat. No. 5,674,328, entitled "Dry tape covered laser shock peening", all of which are assigned to the present Assignee. These applications, as well as others, are in need of efficient quality assurance testing during production runs using laser shock peening.

LSP is a deep treatment of the material and it is desirable to have a quality assurance test that is indicative of a volumetric LSP effect. It is also desirable to have a QA method that is compatible with a dual sided or simultaneous dual sided LSP process wherein substantially equal compressive residual stresses are imparted to both sides of a workpiece, i.e. along the leading edge of a gas turbine engine fan blade.

One laser shock peening quality assurance technique previously used is high cycle fatigue (HCF) testing of blades having leading edges which are LSP'd and notched in the LSP'd area before testing. This method is destructive of the test piece, fairly expensive and time consuming to carry out, and significantly slows production and the process of qualifying LSP'd components. An improved quality assurance method of measurement and control of LSP that is a non-destructive evaluation (NDE), inexpensive, accurate, and quick is highly desirable. It is also desirable to have an NDE quality assurance method that is relatively inexpensive and sufficiently economical to be used on each workpiece instead of a sampling of workpieces. LSP is a process that, as any production technique, involves machinery and is time consuming and expensive. Therefore, any techniques that can reduce the amount or complexity of production machinery and/or production time are highly desirable.

Interferometric profilometry method and apparatus to obtain volumetric data of a single laser shock peened test dimple created with a single firing of a laser used in the laser shock peening process is disclosed in U.S. Pat. No. 5,948,293 "Laser shock peening quality assurance by volumetric analysis of laser shock peened dimple". Other QA methods are disclosed in U.S. Pat. No. 5,987,991 "Determination of Rayleigh wave critical angle"; U.S. Pat. No. 5,974,889 "Ultrasonic multi-transducer rotatable scanning apparatus and method of use thereof"; and U.S. Pat. No. 5,951,790 "Method of monitoring and controlling laser shock peening using an in plane deflection test coupon".

SUMMARY OF THE INVENTION

A method for quality control testing of a laser shock peening process of a production workpiece includes (a) ultrasonically scanning at least a portion of a laser shock peened surface on the workpiece wherein a region having deep compressive residual stresses imparted by the laser shock peening process extends into the workpiece from the laser shock peened surface, (b) digitizing a signal derived from the scanning and forming a digitized image of intensity values from the scanning, (c) calculating at least one statistical function value for a plurality of points of the digitized image of the workpiece based on the intensity values, and (d) comparing the statistical function value to a pass or fail criteria for quality assurance of the laser shock peening process or accepting or rejecting the workpiece.

In one exemplary embodiment of the invention the plurality of points of the digitized image (44) are delineated by a group of circles corresponding to laser shock peened dimples within the portion of the laser shock peened surface. The statistical function comprises at least one of four statistical properties of the digitized image defined by four equations, a Mean Matrix MM(k) for each kth dimple, a Dimple Standard Deviation Matrix SDM(k), a Mean Vector MV(x) of all the points in the group of circles, where x is the number of pixels in each dimple, and a Standard Deviation Vector SDV(x) of each of the group of circles. Three types of the statistical function are a Mean of Dimple Mean Matrix F1, a Mean of Standard Deviation Matrix F2, and a Mean of Standard Deviation Vector F3.

In another exemplary embodiment of the invention the plurality of points of the digitized image are delineated by a rectangle around laser shock peened dimples within a portion of the laser shock peened surface and the statistical function is a Sobel Function F4 including a Sobel operator.

The pass or fail criteria is based on a pre-determined correlation of test piece statistical function data and high cycle fatigue failure based on high cycle fatigue tests of test pieces that were laser shock peened in the same or similar laser shock peenin apparatus. Each of the test pieces has a failure precipitating flaw within a laser shock peened area of the test piece that was laser shock peened in the same or similar laser shock peening apparatus.

BRIEF DESCRIPTION OF THE DRAWINGS

The foregoing aspects and other features of the invention are explained in the following description, taken in connection with the accompanying drawings where:

FIG. 2 is a perspective view illustration of a production fan blade exemplifying a laser shock peened production workpiece used in an exemplary embodiment of the present invention.

FIG. 3 is a cross-sectional view illustration of the fan blade through 3—3 in FIG. 2.

FIG. 8 is an illustration of a four statistical properties used to analyze the intensity data of the points in FIG. 4.

FIG. 9 is an illustration of four exemplary statistical function used to analyze the intensity data of the points in FIGS. 4 and 6.

DETAILED DESCRIPTION

Figure 1:
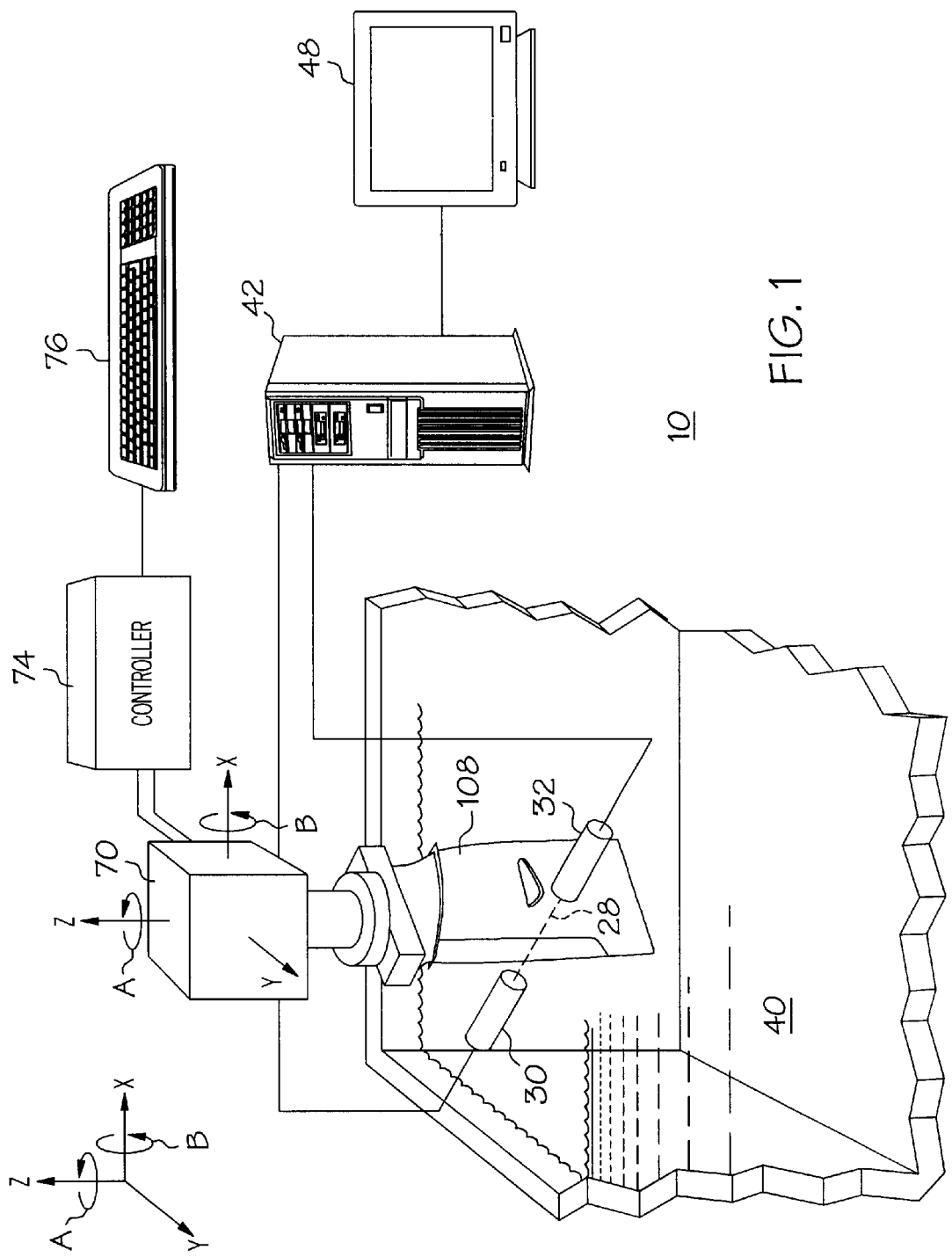
FIG. 1 is a diagrammatic illustration of an ultrasonic system set up for ultrasonically scanning and producing an ultrasonic intensity image of a portion of a laser shock peened patch of a fan blade for use in an exemplary embodiment of the method of the present invention.

Quality assurance is typically a go or no go, pass or fail, accept or reject type of analysis. The method and techniques of the present invention involves quality assurance of the laser shock peening process on a production workpiece such as an exemplary aircraft turbofan gas turbine engine production fan blade 108 illustrated in FIGS. 1, 2, and 3. Blustrated in FIG. 1 is a diagrammatic representation of an ultrasonic scanning system 10 used to perform a quality assurance method for quality control of a laser shock peening process. The method and techniques of the present invention involves quality assurance of a laser shock peening process on a production workpiece such as an exemplary aircraft turbofan gas turbine engine fan blade 108 or other object made of a metallic material as disclosed in U.S. Pat. Nos. 5,492,447, 5,674,329, 5,674,328, and 5,591,009. The methods of the present invention are tests performed during or after laser shock peening of each workpiece, or after or before a batch of workpieces are laser shock peened. During production runs, one or more functions of ultrasonic intensity data is compared to pre-determined pass/fail criteria such as a high cycle fatigue correlation for passing or failing the workpieces.

Referring to FIGS. 2 and 3, the production fan blade 108 includes an airfoil 134 extending radially outward from a blade platform 136 to a blade tip 138 and a root section 140 extending radially inward from the platform 136. The root section 140 has a blade root 142 connected to the platform 136 by a blade shank 144. The airfoil 134 extends in a chordwise direction between a leading edge LE and a trailing edge TE of the airfoil. The fan blade 108 has a leading edge section 150 that extends along the leading edge LE of the airfoil 134 from the blade platform 136 to the blade tip 138. The airfoil 134 has a pressure side 146 and a suction side 148 extending between the leading edge and trailing edges LE and TE of the airfoil. The leading edge section 150 includes a pre-determined first width W such that the leading edge section 150 encompasses an area where nicks and tears that may occur along the leading edge of the airfoil 134 during engine operation. The airfoil 134 subject to a significant tensile stress field due to centrifugal forces generated by the fan blade 108 rotating during engine operation. The airfoil 134 is also subject to vibrations generated during engine operation and the nicks and tears operate as high cycle fatigue stress risers producing additional stress concentrations around them.

To counter fatigue failure of portions of the blade along possible crack lines that can develop and emanate from the nicks and tears, a laser shock peened patch 145 is placed along a portion of the leading edge LE where incipient nicks and tears may cause a failure of the blade due to high cycle fatigue. Within the laser shock peened patch 145, at least one of or both, as illustrated herein, the pressure side 146 and the suction side 148 are simultaneously laser shock peened to form pressure side and suction side laser shock peened surfaces 153 and 154 and corresponding pressure side and suction side pre-stressed regions 155 and 156, respectively, having deep compressive residual stresses imparted by laser shock peening (LSP) extending into the airfoil 134 from the laser shock peened surfaces as seen in FIG. 2. The pre-stressed regions are illustrated along only a portion of the leading edge section 150 but may extend along the entire leading edge LE or longer portion thereof if so desired.

Figures 10, 11:
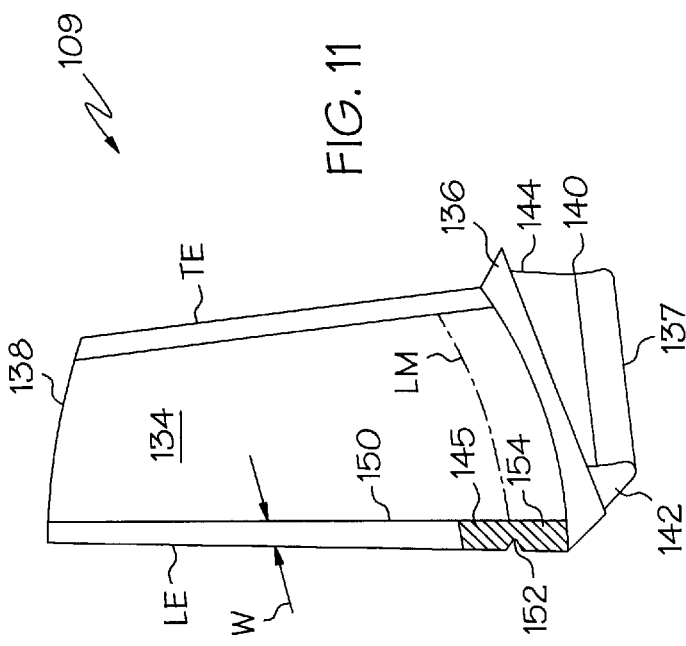
FIG. 10 is an illustration of the Sobel operator used in the Sober statistical function F4 in FIG. 9.
FIG. 11 is a perspective view of a test fan blade exemplifying a test piece which is used to determine a correlation between high cycle fatigue failure and the exemplary statistical functions.

The pre-determined criteria of the exemplary embodiment is based on a correlation of one or more functions of ultrasonic intensity data versus high cycle fatigue data of test versions of the workpieces that are exemplified by laser shock peened and notched test fan blades 109 illustrated in FIG. 11. The production and test blades fan 108 and 109, respectively, are laser shock peened the same way during production runs and HCF testing runs for the correlation.

Illustrated in FIG. 1 is a schematic representation of an ultrasonic scanning system 10 used to perform a quality assurance method for quality control of a laser shock peening process. The system 10 is used for production and test workpieces exemplified by the production fan blade 108 having a laser shock peened patch 145 illustrated in greater detail in FIG. 2. The method includes ultrasonically scanning at least a portion of the patch 145, measuring an ultrasonic signal, digitizing the ultrasonic signal and recording the digitized ultrasonic intensity data, calculating at least one statistical function of digitized ultrasonic intensity data derived from the intensity ultrasonic signal, and comparing the statistical function or functions to a high cycle fatigue correlation of the same type of statistical function or functions to decide whether the laser shocking process or laser shock peened article is acceptable.

An exemplary embodiment of the invention illustrated in FIG. 1 uses ultrasonic scanning and the ultrasonic scanning system 10 includes an ultrasonic transmitting transducer 30 to pass the ultrasonic beam 28 through the fan blade 108 within the bounds of the laser shock peened patch 145 to an ultrasonic receiving transducer 32. The fan blade 108 is mounted on a carrier 70 and a portion of the blade with the laser shock peened patch 145 is submerged in an ultrasonic medium 40 such as water. The carrier 70 is operated to move the fan blade 108 such that the ultrasonic beam 28 from the ultrasonic transmitting transducer 30 passes through the laser shock peened patch 145 to an ultrasonic receiving transducer 32 while a computer 42 or other recording device records electronic signals from the receiving transducer as a function of material density and morphology of the dimples caused by the laser shock peening impact on the patch. The carrier 70 has a multi axis motive means for translating the fan blade 108 in the X, Y and Z directions as well as rotating the fan blade about A and B axes as indicated to position the blade relative to the fixed ultrasonic beam 28, and ultrasonic transmitting transducer and ultrasonic receiving transducers 30 and 32. The movement of the carrier 70 may be controlled by a controller 74 with the use of a keyboard 76 operated by a user.

The recorded electronic signals are converted into an ultrasonic intensity image 44 that is stored in a computer 42 and can be displayed on a screen 48 of the computer 42 as illustrated in FIG. 3. The invention in its broader aspects can use different types of emissions which are processed with the computer and recorded in a computerized array of values or in the digitized ultrasonic intensity image 44 as a plurality of pixels 46 illustrated in FIG. 3 which is then analyzed with statistical functions.

The exemplary embodiment illustrated herein uses pixel data derived from recorded intensity data from the scanning of the patch 145 with the ultrasonic beam 20. Illustrated in FIG. 3 is a digital image depicting ultrasonic intensity data in pixel format from a scan of the laser shock peened patch 145 in FIGS. 1 and 2. Eight virtual circles 80 surrounding a portion of the plurality of pixels 46 are chosen to delineate the pixel data used in one embodiment of the statistical analysis of the present invention. Each of the virtual circles 80 corresponds to one of the laser shock peened circular dimples 158. If the dimples are not circular then other virtual shapes may be used as alternatives to the virtual circles. More or less than eight virtual shapes or circles may be used.

Figure 4:
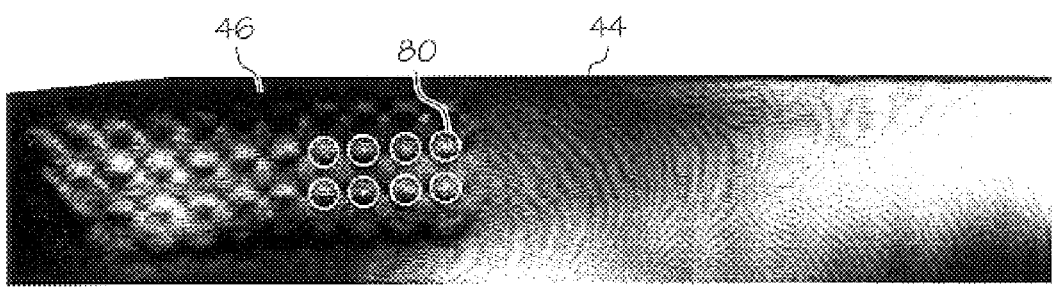
FIG. 4 is an illustration of a computer screen depicting ultrasonic intensity data from a scan of a laser shock peened patch in FIG. 2 and virtual circles delineating data used in some of the embodiments of the present invention.
Figure 5:
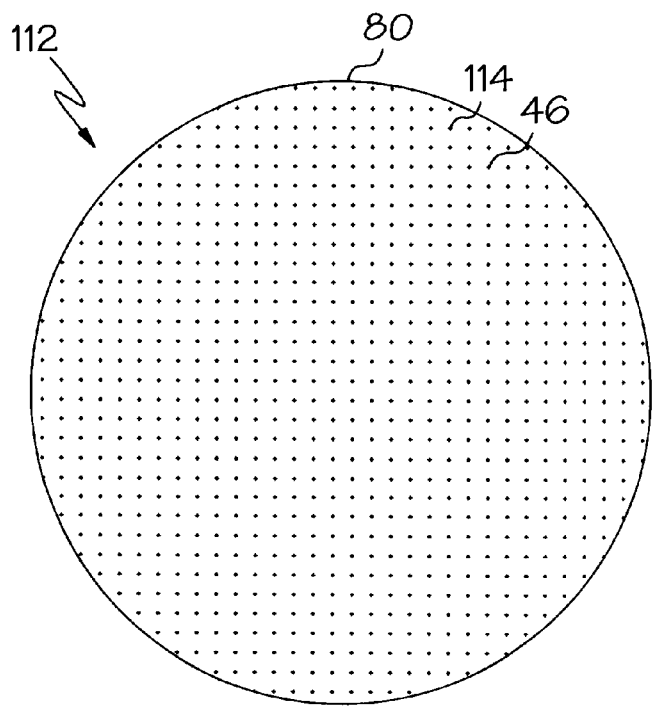
FIG. 5 is an illustration of points in one of the virtual circles of the intensity data in FIG. 4 that are used to compute some of statistical functions.

FIG. 5 is an illustration of an array 112 of points 114 in the virtual circle 80 that are used to analyze the intensity data from FIG. 4 and to compute statistical functions from the intensity data illustrated in FIG. 4. The results of the computed statistical functions from the intensity data are compared to a high cycle fatigue correlation of the same type of statistical function or functions to decide whether the laser shocking process or laser shock peened article is acceptable.

The statistical functions exemplified herein use four statistical properties of the digitized ultrasonic intensity images 44. Equations in FIG. 8 define these statistical properties as follows: a Mean Matrix MM(k) for each kth dimple (illustrated for K=8 dimples per blade); a Dimple Standard Deviation Matrix SDM(k); a Mean Vector MV(x) for each xth pixel in each dimple and where X is the total number of points or pixels in each dimple (illustrated as 377 pixels); and a Standard Deviation Vector SDV(x).

Equations in FIG. 9 define four alternative statistical functions (F1–F4) each of which is suitable for use in the analysis of the present invention. Each of the statistical functions (F1–F4) is calculated for each workpiece or blade. The first statistical function is a Mean of Dimple Mean Matrix F1, and is computed using one or more rows of the dimples up to and including all the dimples. The exemplar embodiment used herein uses four of the dimples per row and 2 of the rows of dimples are per blade. Thus, there are 8 dimples per blade and 377 pixel points within each of the dimples and, therefore, the function is summed over k=1–8 and x=1–377. A measured variable is dk(x) is a pixel intensity within kth dimple. First, 377 pixel intensity values dk(x) for each dimple (x) is summed and the resulting eight dimple sums are summed resulting in a total sum. The Mean of Dimple Mean Matrix F1 is then computed for each blade by dividing total sum by K which is the number of dimples (x).

The second statistical function is a Mean of Standard Deviation Matrix F2 and is computed using one or more rows of the dimples up to and including all the dimples. The exemplary embodiment used herein uses four of the dimples per row and 2 of the rows of dimples are per blade. Again illustrated herein is four dimples per row and 2 rows are per blade and each dimple having 377 pixel points. A Standard Deviation (SD) for 377 pixels is calculated for each of the K dimples then the K SDs are summed and that sum is divided by the total number of dimples K.

The third statistical function is a Mean of Standard Deviation Vector F3 and is computed using one or more rows of the dimples up to and including all the dimples. The exemplary embodiment used herein uses four of the dimples per row and 2 of the rows of dimples are per blade. It assumes that four dimples per row and 2 rows are per blade which are 8 dimples. Each dimple has 377 pixel points. First, a Standard Deviation Vector (SDV) for the 8 dimples is calculated for each of the 377 pixels then the 377 SDVs are summed and that sum is divided by 377 which is the total number of points.

Figure 7:
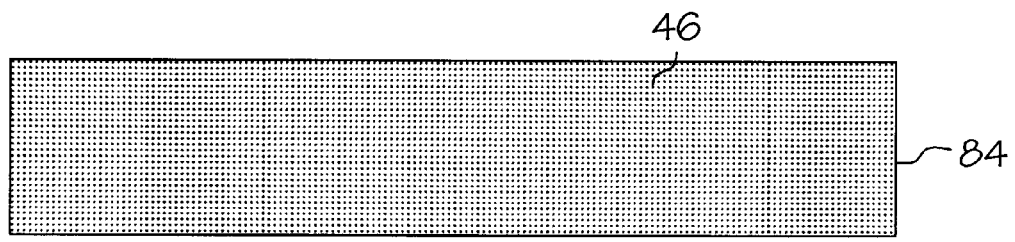
FIG. 7 is an illustration of points in the virtual rectangle the intensity data in FIG. 6 that is used with a Sobel operator statistical function.

Illustrated in FIG. 7 is the digital image depicting the ultrasonic intensity data in pixel format from a scan of the laser shock peened patch 145 in FIGS. 1 and 2, a portion of the plurality of pixels 46, the virtual circles 80 bounded by a virtual rectangle 84. The virtual rectangle 84 is used to delineate pixel data used with a fourth statistical function, a Sobel function F4 illustrated in FIG. 9. The exemplar embodiment as illustrated herein uses a virtual rectangle 84 that encompasses three of the dimples per row and three of the rows of dimples are per blade. In the equation of the Sobel Function F4, i and j are x and y directional points within the rectangle 84 in FIG. 3. An exemplary area of the rectangle shown in FIG. 3 is 2 inches by ½ inch. The rectangle 84 is two inches long in the x direction and ½ inch long in the y direction. Pixels intensities in the rectangle were broken up into 250×50 points such that i=1–250 and j =1–50.

The function du,v=pixel value at the nine points u,v for each point i,j and the function wu,v=the Sobel operator at u,v which is illustrated in FIG. 10. In the exemplary embodiment used herein, a 3×3 Sobel operator W, the variables u,v are positions in an array that includes the point i,j and the 8 surrounding points in the array of pixels in the image such that u=1 to 3 and v=1 to 3. A scaling factor N (10,000 was used in the exemplary embodiment) is used to make F4 a low number that is easy to work with. Sobel operators are well known for use in edge detection and image enhancement techniques using pixel intensity data. The Sobel operator used herein is a 3×3 non-linear edge enhancement.

Figure 6:
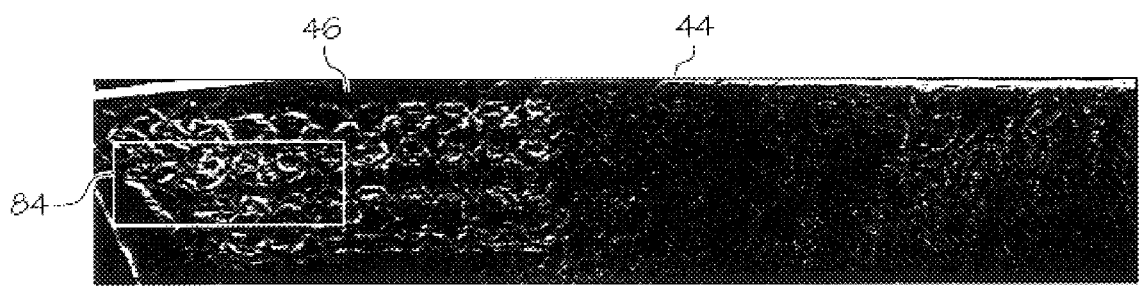
FIG. 6 is an illustration of the computer screen in FIG. 2 with a virtual rectangle surrounding a set ultrasonic intensity data used in with a Sobel operator statistical function.

The Sobel operator W, as illustrated in FIG. 10, is in the form of a three by three operator array that multiplies a specific pixel intensity D by zero which is the center number in the array as designated by numeral 51. It then multiplies all surrounding pixels intensities by a −1, −2, −1, 0, 1, 2, 1, and 0 respectively from left to right in a counter-clockwise fashion, as shown in FIG. 6. The summation of all of these multiplied values is the new replacement value for this specific pixel intensity of interest. If there are no spatial discontinuities from top to bottom, then the pixels above, the pixel of interest, will be multiplied by a negative number that is equivalent to the multipliers below the pixel of interest. Therefore, if the pixel numbers are relatively the same, the summation will be close to zero.

The high cycle fatigue (HCF) correlation of the test fan blades 109 illustrated herein is based on fatigue testing of laser shock peened and notched test fan blades 109 as illustrated in FIG. 11, that are full scale and notched to precipitate a failure. The test pieces or test fan blades 109 are made the same way as the actual production fan blades 108 with a notch 152 added after the test blade 109 is laser shock peened to form the patch 145.

The laser shock peened test fan blades 109 are ultrasonically scanned and the digitized ultrasonic intensity data stored for statistical analysis. The HCF testing ma be used to establish pass/fail criteria for use during production runs to be compared to the results of the statistical analysis from ultrasonic scanning and statistical analysis of the digitized ultrasonic intensity data from the scanning. The digitized ultrasonic intensity data is recorded and analyzed for correlation purposes. The laser shock peened test fan blades 109 are vibrated at its first mode frequency until it fails. A number of test fan blades 109 or just one test blade 109 may be notched and subjected to high cycle fatigue tests to establish the correlation. For high cycle fatigue, each laser shock peened test fan blade 109 has a notch 152, representing a failure precipitating flaw, placed in the laser shock peened patch 145. The notch 52 is placed at a predetermined position of the pre-stressed regions 155 and 156 after the blade is laser shock peened. The notch 152 may be centered about a predetermined mode line such as a first mode line LM. If tested blade meets standards or test criteria on length of time and amplitude of the forcing function that is exiting the blade, then it is acceptable. These results can then be used during production runs to qualify the laser shock peening process. It is contemplated that one calibration can be used for an entire production run as long as the production laser shock peening parameters do not change.

Figure 12:
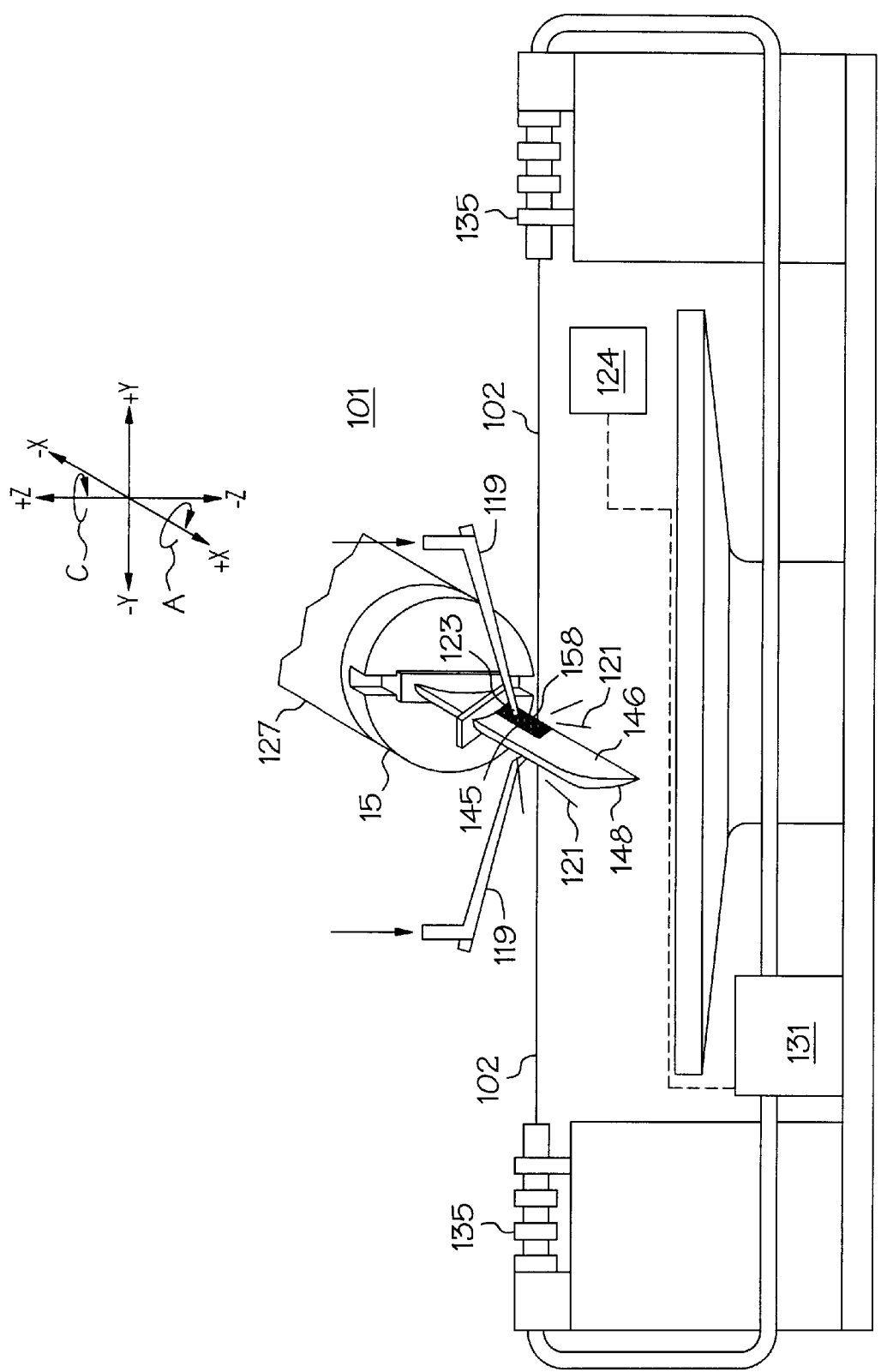
FIG. 12 is a schematic perspective illustration of the blade in FIGS. 1 and 2 mounted in a laser shock peening system.

Illustrated in FIG. 12 is a laser shock peening apparatus and system 101 for laser shock peening the fan blade 108. The fan blade 108 is mounted in the fixture 15 which is attached to a five-axis computer numerically controlled (CNC) manipulator 127. Five axes of motion illustrated in the exemplary embodiment are conventional translational axes X, Y, and Z, and conventional rotational axes A and C which are well known in CNC machining. The manipulator 127 moves and positions the production and test production fan blades 108 and 109 to effect laser shock peenin on the fly. Laser shock peening may be done in a number of various ways using paint or tape as an ablative medium (see U.S. Pat. No. 5,674,329 entitled "Adhesive Tape Covered Laser Shock Peening"). The same laser shock peening apparatus and system 101 is used in the laser shock peening process of the leading edge section 150 of the production fan blade 108 and the test fan blades 109 (representing the test pieces and workpieces).

The area to be laser shock peened and form the laser shock peened patch 145, the pressure and suction side laser shock peened surfaces 153 and 154 are covered with an ablative coating such as paint or adhesive tape to form a coated surface as disclosed in U.S. Pat. Nos. 5,674,329 and 5,674,328. The coating provides an ablative medium over which is a clear containment medium which may be a clear fluid curtain such as a curtain of flowing water 121.

The laser beam shock induced deep compressive residual stresses may be produced by repetitively firing two high power laser beams 102, each of which is defocused ± a few mils with respect to the coated pressure side and suction side laser shock peened surfaces 153 and 154 of the pressure side 146 and the suction side 148 of the production fan blade 108. Each of the laser beams is fired through the curtain of flowing water 121 supplied by a conventional water nozzle 123 at the end of a conventional water supply tube 119. The curtain of flowing water 121 is flowed over the coated surfaces. The coating is ablated generating plasma which results in shock waves on the surface of the material. Other ablative materials may be used to coat the surface as suitable alternatives to paint. These coating materials include metallic foil or adhesive plastic tape as disclosed in U.S. Pat. Nos. 5,674,329 and 5,674,328. These shock waves are re-directed towards the coated surfaces by the curtain of flowing water 121 to generate travelling shock waves (pressure waves) in the material below the coated surfaces. The amplitude and quantity of these shock waves determine the depth and intensity of compressive stresses. The ablative coating is used to protect the target surface and also to generate plasma. The ablative coating is used to protect the target surface and also to generate plasma. The laser beam shock induced deep compressive residual stresses in the compressive pre-stressed regions are generally about 50–150 KPSI (Kilo Pounds per Square Inch) extending from the laser shock peened surfaces to a depth of about 20–50 mils into the pre-stressed regions.

The production fan blade 108 is continuously moved while the stationary high power laser beams 102 are continuously firing through the curtain of flowing water 121 on the coated pressure and suction side laser shock peened surfaces 153 and 154 and forming spaced apart laser shock peened circular spots or dimples 158. The production fan blades 108 are laser shock peened the same way during production runs and HCF testing runs for the correlation. A controller 124 is used to modulate and control the laser shock peening system 101 to fire the laser beams 102 on the coated surfaces in a controlled manner. Ablated coating material is washed out by the curtain of flowing water 121.

The embodiment of the method of the present invention illustrated herein includes continuously moving the blade while continuously firing the laser beam on the taped surface and adjacent laser shock peened circular spots may be hit in different sequences. However, the laser beam may be moved instead just so long as relative movement between the beam and the surface is effected.

While there have been described herein what are considered to be preferred and exemplary embodiments of the present invention, other modifications of the invention shall be apparent to those skilled in the art from the teachings herein and, it is therefore, desired to be secured in the appended claims all such modifications as fall within the true spirit and scope of the invention. Accordingly, what is desired to be secured by Letters Patent of the United States is the invention as defined and differentiated in the following claims.

What is claimed is:

1. A method for quality control testing of a laser shock peening process of a production workpiece, said method comprising:

(a) ultrasonically scanning at least a portion of a laser shock peened surface on the workpiece wherein a region having deep compressive residual stresses imparted by the laser shock peening process extends into the workpiece from the laser shock peened surface, (b) digitizing a signal derived from said scanning and forming a digitized image of intensity values from the scanning, (c) calculating intensity values for a plurality of points of the digitized image and calculating at least one statistical function value of at least one statistical function of the workpiece based on the intensity values, and (d) comparing the statistical function value to a pass or fail criteria for quality assurance of the laser shock peening process or accepting or rejecting the workpiece.

2. A method as claimed in claim 1 wherein the plurality of points of the digitized image are delineated by a group of circles corresponding to laser shock peened dimples within the portion of the laser shock peened surface.

3. A method as claimed in claim 2 wherein the scanning and emissions are ultrasonic pass through types performed with transmitting and receiving transducers on opposite sides of the workpiece.

4. A method as claimed in claim 2 wherein:

the statistical function comprises at least one of four statistical properties of the digitized image, the four statistical properties are defined by four equations, the first equation is a Mean Matrix $$MM(k) = \frac{1}{X}\sum_{x=1}^{X} d_k(x),$$

wherein d is the intensity value for each xth point in each kth dimple, summed over X number of pixels or points in each of the circles, the second equation is a Dimple Standard Deviation Matrix $$SDM(k) = \sqrt{\frac{1}{X}\sum_{x=1}^{X}(d_k(x) - MM(k))^2},$$

the third equation is a Mean Vector $$MV(x) = \frac{1}{K}\sum_{k=1}^{K} d_k(x),$$

and the fourth equation is a Standard Deviation Vector $$SDV(x) = \sqrt{\frac{\sum_{x=1}^{X}(d_k(x) - MV(x))^2}{X}}$$

of each of the group of circles.

5. A method as claimed in claim 4 wherein the statistical function is a Mean of Dimple Mean Matrix $$F1 = \frac{1}{K}\sum_{k=1}^{K} MM(k) = \frac{1}{K}\sum_{k=1}^{K}\left[\frac{1}{X}\sum_{x=1}^{X} d_k(x)\right].$$

6. A method as claimed in claim 4 wherein the statistical function is a Mean of Standard Deviation Matrix $$F2 = \frac{1}{K}\sum_{k=1}^{K} SDM(k) = \frac{1}{K}\sum_{k=1}^{K}\left[\sqrt{\frac{1}{X}\sum_{x=1}^{X}(d_k(x) - MM(k))^2}\right].$$

7. A method as claimed in claim 4 wherein the statistical function is a Mean of Standard Deviation Vector $$F3 = \frac{1}{X}\sum_{x=1}^{X} SDV(x) = \frac{1}{X}\sum_{x=1}^{X}\left[\sqrt{\frac{\sum_{k=1}^{K}(d_k(x) - MV(x))^2}{K}}\right].$$

8. A method as claimed in claim 1 wherein:

the plurality of points of the digitized image are delineated by a rectangle around laser shock peened dimples within a portion of the laser shock peened surface and the statistical function is a Sobel Function $$F4 = \frac{\sum_i \sum_j (d_{u,v} * w_{u,v})}{N},$$

wherein w is a Sobel operator, the function F4 is summed over i and j which correspond to x and y directional points within the rectangle, du,v are intensity values at nine points u,v for each point i,j, and N is a scaling factor.

9. A method as claimed in claim 8 wherein the Sobel operator $$W_{u,v} = \begin{vmatrix} w_{1,1} & w_{1,2} & w_{1,3} \\ w_{2,1} & w_{2,2} & w_{2,3} \\ w_{3,1} & w_{3,2} & w_{3,3} \end{vmatrix} = \begin{vmatrix} -1 & -2 & -1 \\ 0 & 0 & 0 \\ 1 & 2 & 1 \end{vmatrix}.$$

10. A method as claimed in claim 1 wherein the pass or fail criteria is based on a predetermined correlation of test piece statistical function data and high cycle fatigue failure based on high cycle fatigue tests of test pieces that were laser shock peened in the same or similar laser shock peening apparatus.

11. A method as claimed in claim 10 wherein the test pieces each have a failure precipitating flaw within a laser shock peened area of the test piece that was laser shock peened in the same or similar laser shock peening apparatus.

12. A method as claimed in claim 11 wherein the plurality of points of the digitized image are delineated by a group of circles corresponding to laser shock peened dimples within the portion of the laser shock peened surface.

13. A method as claimed in claim 12 wherein the scanning and emissions are ultrasonic pass through types performed with transmitting and receiving transducers on opposite sides of the workpiece.

14. A method as claimed in claim 12 wherein:

the statistical function comprises at least one of four statistical properties of the digitized image, the four statistical properties are defined by four equations, the first equation is a Mean Matrix $$MM(k) = \frac{1}{X} \sum_{x=1}^{X} d_k(x),$$

wherein d is the intensity value for each xth point in each kth dimple, summed over X number of pixels or points in each of the circles, the second equation is a Dimple Standard Deviation Matrix $$SDM(k) = \sqrt{\frac{1}{X} \sum_{x=1}^{X} (d_k(x) - MM(k))^2},$$

the third equation is a Mean Vector $$MV(x) = \frac{1}{K} \sum_{k=1}^{K} d_k(x),$$

and the fourth equation is a Standard Deviation Vector $$SDV(x) = \sqrt{\frac{\sum_{x=1}^{X}(d_k(x) - MV(x))^2}{X}}$$

of each of the group of circles.

15. A method as claimed in claim 14 wherein the statistical function is a Mean of Dimple Mean Matrix $$F1 = \frac{1}{K} \sum_{k=1}^{K} MM(k) = \frac{1}{K} \sum_{k=1}^{K} \left[ \frac{1}{X} \sum_{x=1}^{X} d_k(x) \right].$$

16. A method as claimed in claim 14 wherein the statistical function is a Mean of Standard Deviation Matrix $$F2 = \frac{1}{K} \sum_{k=1}^{K} SDM(k) = \frac{1}{K} \sum_{k=1}^{K} \left[ \sqrt{\frac{1}{X} \sum_{x=1}^{X} (d_k(x) - MM(k))^2} \right].$$

17. A method as claimed in claim 14 wherein the statistical function is a Mean of Standard Deviation Vector $$F3 = \frac{1}{X} \sum_{x=1}^{X} SDV(x) = \frac{1}{X} \sum_{x=1}^{X} \left[ \sqrt{\frac{\sum_{k=1}^{K} (d_k(x) - MV(x))^2}{K}} \right].$$

18. A method as claimed in claim 11 wherein:

the plurality of points of the digitize d image are delineated by a rectangle around laser shock peened dimples within a portion of the laser shock peened surface and the statistical function is a Sobel Function $$F4 = \frac{\sum_i \sum_j (d_{u,v} * w_{u,v})}{N},$$

wherein w is a Sobel operator, and the function F4 is summed over i and j which correspond to x and y directional points within the rectangle, du,v are intensity values at nine points u,v for each point i,j, and N is a scaling factor.

19. A method as claimed in claim 18 wherein the Sobel operator $$W_{u,v} = \begin{vmatrix} w_{1,1} & w_{1,2} & w_{1,3} \\ w_{2,1} & w_{2,2} & w_{2,3} \\ w_{3,1} & w_{3,2} & w_{3,3} \end{vmatrix} = \begin{vmatrix} -1 & -2 & -1 \\ 0 & 0 & 0 \\ 1 & 2 & 1 \end{vmatrix}.$$

* * * * *